United States Patent [19]

Averette

[11] Patent Number: 4,736,639

[45] Date of Patent: Apr. 12, 1988

[54] AUTOMATIC FLUID INJECTOR

[75] Inventor: Julius P. Averette, Baker, La.

[73] Assignee: Dynatch Precision Sampling Corporation, Baton Rouge, La.

[21] Appl. No.: 1,198

[22] Filed: Jan. 7, 1987

[51] Int. Cl.[4] ............................................. G01N 35/06
[52] U.S. Cl. ................................ 73/864.24; 73/863.81
[58] Field of Search ......................... 73/864.24, 863.81

[56] References Cited

U.S. PATENT DOCUMENTS 3,885,438  5/1975  Harris, Sr. et al. .............. 73/863.81

Primary Examiner—Thomas P. Noland
Attorney, Agent, or Firm—Llewellyn A. Proctor

[57] ABSTRACT

An improved automatic fluid injector is described which includes generally (A) a syringe, or syringe assembly, inclusive of a barrel of relatively large diameter into which a fluid specimen can be loaded, and fluid specimen displaced from the barrel into the inlet of an analytical instrument, (B) an injector feed assembly for the pick up and of a fluid specimen for delivery to the barrel of the syringe, and (C) a magazine for transporting fluid specimen-containing vials for pick up by the injector feed assembly. The combination is one wherein the syringe assembly is integral with a carriage upon which it is mounted, the carriage providing a mechanism for loading a fluid specimen delivered from a vial via the injector feed assembly into the large diameter barrel without the formation of bubbles, or foam.

14 Claims, 6 Drawing Sheets (# 4,736,639)

AUTOMATIC FLUID INJECTOR

FIELD OF THE INVENTION

This invention relates to improvements in automatic fluid injectors, or automated syringes. In particular, it relates to a syringe of relatively large diameter into which fluid specimens can be loaded without the formation of bubbles, or foam, and the subsequent injection of such specimens.

BACKGROUND AND PROBLEMS

Automated fluid injection devices, particularly automated needle syringes, have gained wide acceptance by industry, universities, and by the scientific and medical communities. This is due in large part to the advantages offered by modern data gathering techniques, and consequent reduction in operating manpower without loss in accuracy.

In the operation of automated fluid injection devices generally, septum covered vials are charged with a fluid specimen and transported in seratim via a magazine to a station adjacent a probe assembly, the probe assembly is projected through the septum of a vial and employed as a conduit to convey a portion of the fluid specimen to the syringe. Within the barrel of the syringe, a quantity of the fluid specimen is measured out and injected via the dispensing end of the syringe into the inlet of the analytical instrument.

Automated fluid injectors are capable of dispensing very small, accurately measured quantities of fluid specimens on the order of a few microliters, generally up to about 10 microliters with high accuracy and precision. When the barrel of a syringe is of quite small inside diameter, generally on the order of about 0.5 millimeter (mm) to about 1 mm inside diameter, the fluid specimen can be loaded into the bore of the syringe such that it is completely filled, without displacement of any portion of the fluid therein by gas or air. When the bore of the syringe can be loaded in this manner a preselected, predetermined amount of the fluid specimen can be displaced from the bore of the barrel with extremely high precision and accuracy. When however the bore of the barrel is greater than about 1 mm in diameter, gas or air often enters into the bore with the fluid specimen, this producing small bubbles or foam which can drastically interfere with the accuracy and precision of such types of automated fluid injector. Albeit the length of the syringe bore can be increased, and the diameter of the bore decreased accordingly to provide the space required for larger volumes of a fluid specimen, this means of decreasing the bore diameter of syringes obviously has serious limitations. Among other reasons, there are some very practical limits in employing syringes of great length, from both the operation and manufacturing point of view. Generally, it is undesirable to build syringes the barrels of which are of length greater than about 60 mm. There is thus a need for automatic fluid injectors capable of employing syringes having barrels with bores with relatively large diameter, and of relatively short length, particularly syringes having barrels with bores of about 1 mm, and greater, into which fluid specimens can be loaded without the presence therein of any significant amount of gas, or air as bubbles, or foam.

OBJECTS

It is, accordingly, a primary object of the present invention to satisfy this need by providing a novel automatic fluid injector, particularly one having as a component of its overall combination a syringe having a barrel the bore of which is of relatively large diameter.

A specific object is to provide apparatus capable of continuously cyclically serially withdrawing liquid specimens from prefilled septum covered vials, and loading with rapidity the specimens in seriatim within the bore of the syringe without an significant contamination of the liquid specimen with gas, or air such as would interfere with the precision, and accuracy of the operation of the automatic fluid injector.

A further, and more specific objective is to provide apparatus of simple and relatively inexpensive construction, particularly apparatus which can be readily serviced and operated, which readily lends itself to rapid mass production techniques.

SUMMARY OF THE INVENTION

These objects and others are achieved in accordance with the present invention which embodies improvements in fluid injector devices, notably automatic fluid injector systems which include the usual combination of (A) a syringe, or syringe assembly inclusive of a barrel into which a fluid specimen can be loaded, and means for the displacement thereof into a media, (B) an injector feed assembly comprised of a probe sub-assembly inclusive of hollow needles, especially a pair of concentrically mounted hollow needles which provide a conduit for the pick up of said fluid specimen from a vial, and transport thereof into the barrel of said syringe, and (C) a magazine for transporting one or more fluid specimen-containing septum sealed vials for pick up by said injector feed probe sub-assembly for delivery to the barrel of said syringe for subsequent injection into said media, e.g. the inlet of an analytical instrument. The apparatus combination of this invention embodies, inter alia, improvements in the syringe, or syringe assembly (A) wherein the barrel thereof is of relatively large internal diameter, especially of diameter equal to or greater than about 1.0 mm, more particularly greater than about 1.1 mm, and of length no greater than about 50 mm, preferably no greater than about 12 mm. The syringe assembly is integral with a carriage upon which it is mounted, the latter providing a means for loading a fluid specimen delivered from a vial via said injector feed assembly into the large diameter barrel thereof without the formation of bubbles, or foam, and subsequent dispensing of the fluid specimen from said barrel into a medium with accuracy, precision, and speed. The overall combination includes both pneumatic and hydraulic means for effecting the necessary sequence of movements necessary for carrying out essential apparatus functions.

The invention, and its principle of operation, will be more fully understood by reference to the following detailed description of a specific and preferred embodiment, and to the attached drawings to which reference is made in the description. In the description similar numbers are used to represent similar parts or components, and subscripts are used with numbers where components are duplicated.

In the drawings:

FIG. 1 depicts a side elevation view of a preferred automatic fluid injector which includes a platform on which is mounted a carriage, reciprocably movable thereupon, which carries (A) a syringe, or syringe assembly (with syringe in closed, or load position) inclusive of a barrel on the the rearward end of which is mounted a valve, and forward end on which is mounted a needle, (B) an injector feed unit, inclusive of its probe assembly which is shown in raised position, and (C) a carrousel type magazine, or feed tray, which carries fluid specimen-containing vials for pick up of specimen therefrom by the probe assembly for delivery to the syringe, or syringe assembly.

FIG. 2 is Section 2—2 of FIG. 1, this view depicting in plan principally the syringe, or syringe assembly, mounted upon its carriage which is reciprocably movable upon the platform of said automatic fluid injector.

FIG. 3 depicts a side elevation view of the automatic fluid injector wherein the syringe, or syringe assembly is depicted in partial section, and the probe assembly of the injector feed unit is shown in lowered position as positioned in withdrawing a fluid specimen from a vial delivered by said magazine, or feed tray, for loading a fluid specimen therefrom into the barrel of the syringe, and the valve and needle portion of the syringe is retracted to its rearward position relative to the carriage within which it is transported for filling without foaming the barrel of the syringes with a portion of the fluid specimen; and FIG 3A is an enlarged fragmentary view which gives some further details of the probe assembly per se.

DETAILED DESCRIPTION OF THE INVENTION

Figure 1:
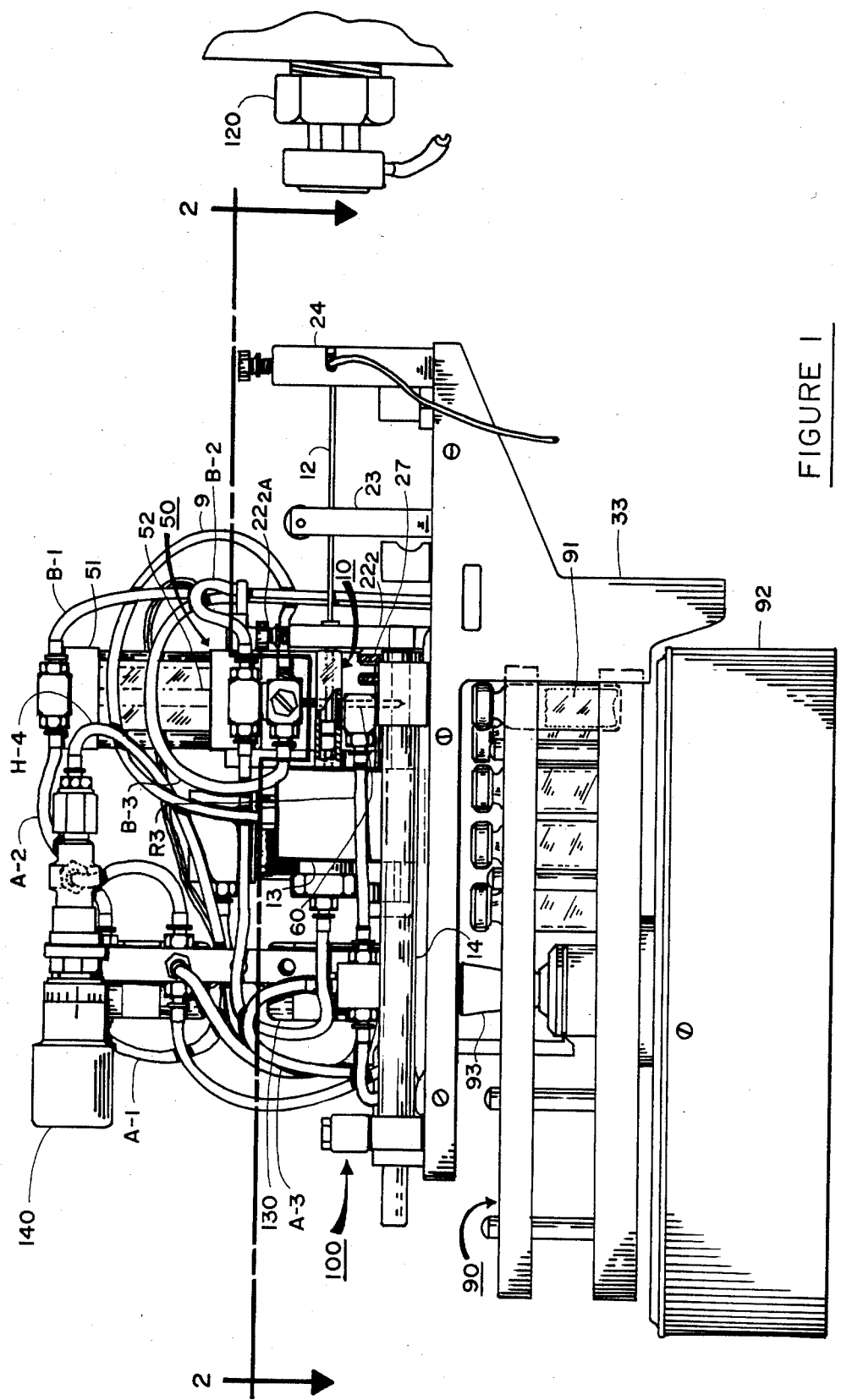
Figure 6:
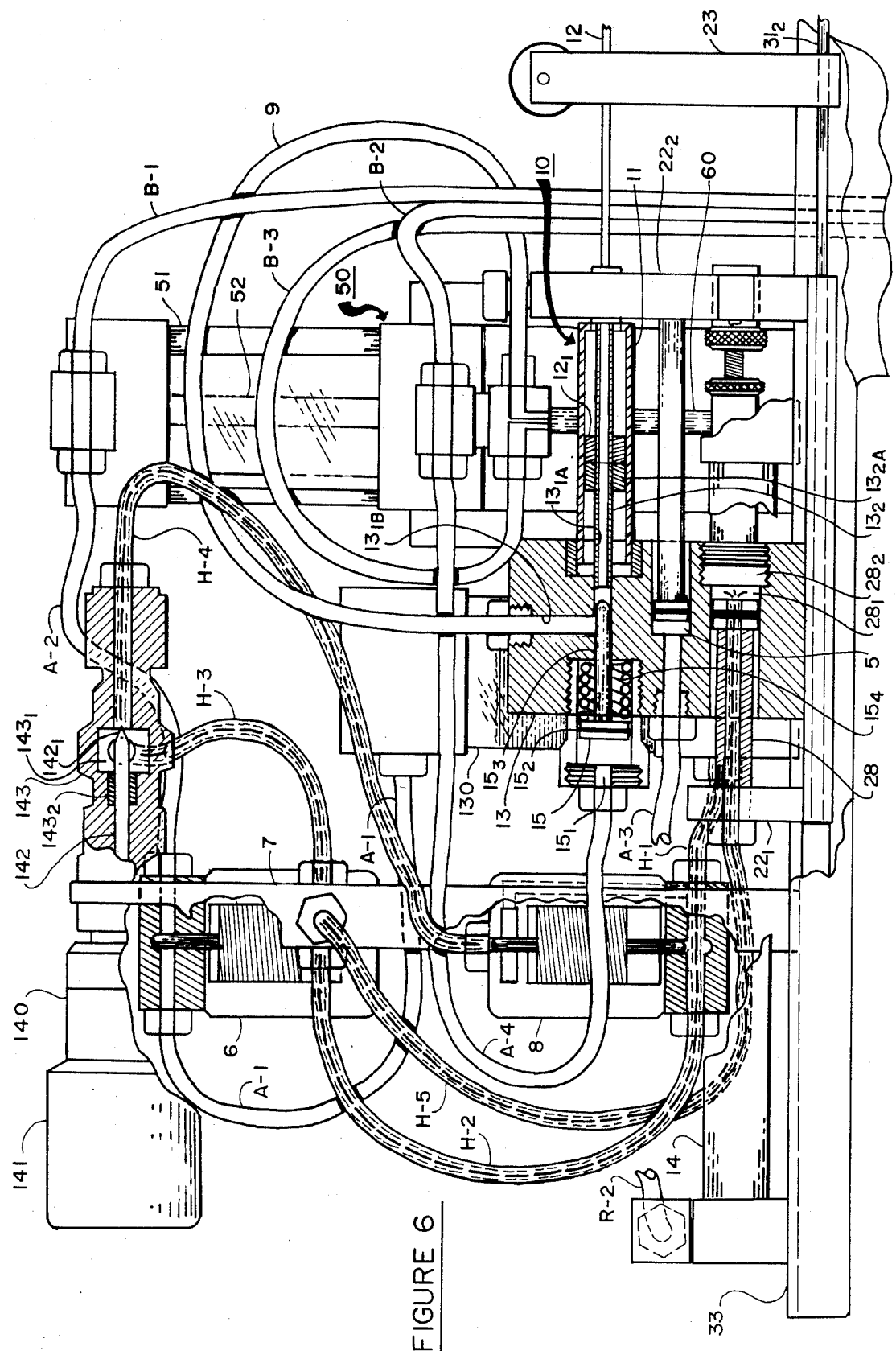
FIG. 6 depicts, via a side elevation view of the automatic fluid injector with appropriate cut-aways, details of the pneumatic and hydraulic system which actuates said automatic fluid injector.

Reference is made to the figures, first generally to FIGS. 1-6 which shows a preferred automatic fluid injector 100. The principle subassemblies of the automatic fluid injector 100 include (A) a syringe, or syringe assembly 10, (B) an injector feed assembly 50, inclusive of a reciprocable probe assembly 60 (or pair of concentric hollow probes), the details of which are best given by reference to FIG. 3A, which is used to pick up a fluid specimen for delivery of same to the syringe, or syringe assembly 10, and (C) a magazine or carrousel type feed tray 90 for transporting one and preferably a plurality of vials of fluid specimens to a location for pick up by said probe assembly 60 of said injector feed assembly 50. Portions of fluid specimens are picked up in serial fashion from the individual vials and injected in seratim in accurately measured quantities into e.g., an inlet 120 of an analytical instrument, via the direct action of the syringe, or syringe sub-assembly 10. The sub-assemblies (A), (B), and (C) may be contained in whole or in part within a casing, housing or framed structure and are responsive to automatic control means such as described in U.S. Pat. No. 3,754,443. The principle features and overall function of these several subassemblies and their relation one to another are generally as follows:

(A) The syringe, or syringe sub-assembly 10, the details of which are best shown by reference to FIG. 6, is constituted of a syringe per se which includes a barrel 11 having a bore of relatively large internal diameter, on one end of which is mounted a cannula, or needle 12, and on the opposite end of which is mounted a valve 13. On the rearward terminal end of the needle 12 is affixed a tubular seal 121 of relatively large diameter which fits snugly and concentrically within the bore of the barrel 11, within which the needle 12 is reciprocably movable via movement of the barrel 11 relative thereto over a limited distance defined by a zero fill position (FIG. 6), and a preselected pre-set maximum fill position (FIGS. 3 and 4). The valve 13 is mounted on the opposite end of the barrel 11. The valve 13 provides an open position and closed position. In its open position the valve 13 can admit a fluid specimen delivered from a vial via action of the probe assembly 60 of the injector feed assembly 50 into the bore of the barrel 11. In its closed position the flow of the fluid specimen into the barrel is interrupted, and fluid specimen is retained within the bore of the barrel 11 for injection via the dispensing end $12_2$ of the needle 12. In its filling and injection function, the bore of barrel 11 of the syringe is filled via specimen fill line 9 through which a fluid specimen is conveyed via the open valve 13, then the valve 13 is closed, the dispensing end $12_2$ of the needle 12 is thrust into a medium, e.g., septum inlet 120, and the valve 13-barrel 11 sub-assembly then moved relative to needle 12 to displace fluid specimen from the barrel 11 through the distal, or dispensing end $12_2$ of the needle 12. The mechanism by which this function is accomplished will be subsequently described.

Figure 2:
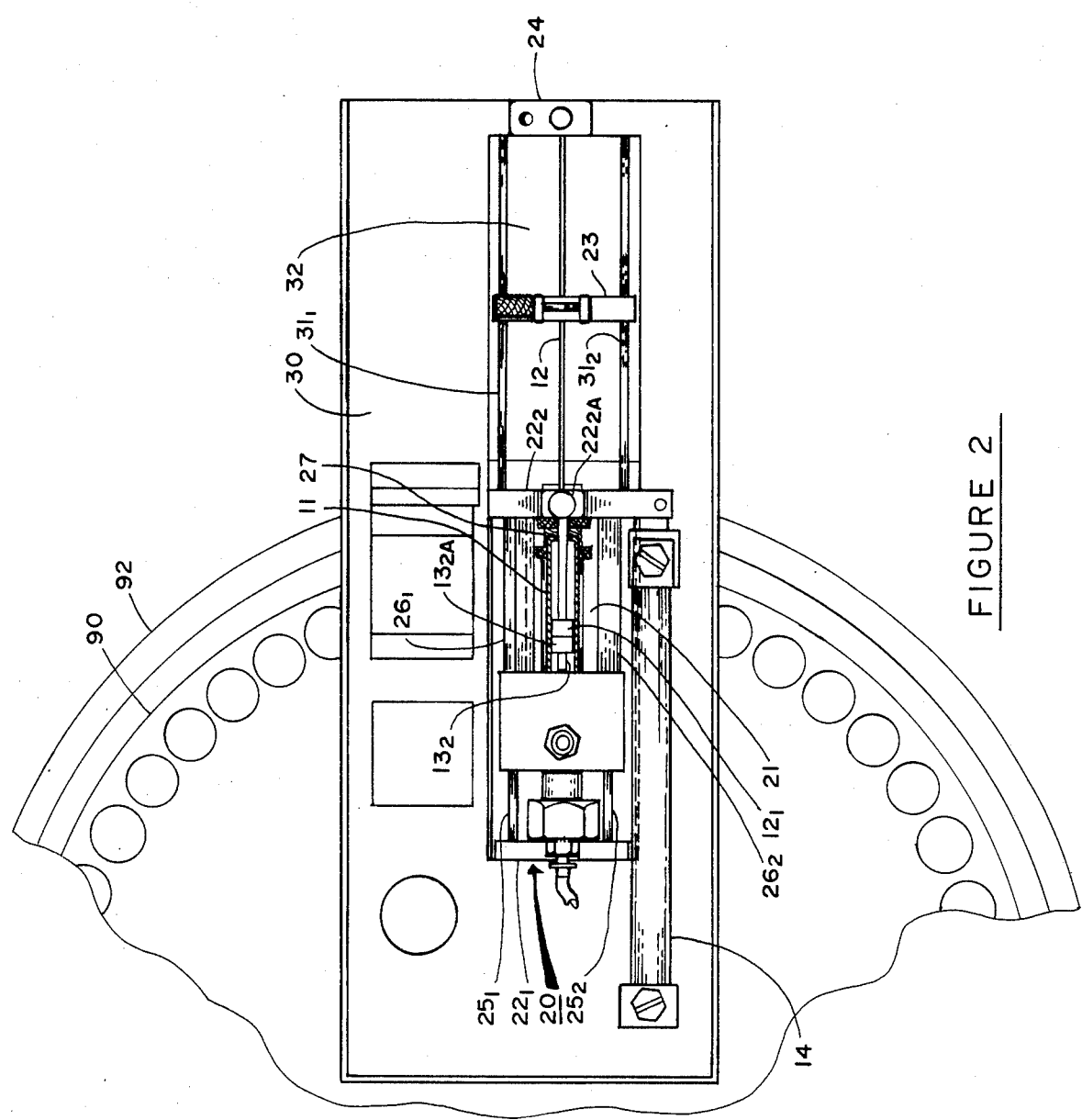

The syringe, or syringe assembly 10 generally, as best shown by reference to FIG. 2, is affixed to and mounted upon a carriage 20, within which the valve 13-barrel 11 sub-assembly is reciprocably movable over a limited preselected, adjustably determined distance; and the carriage 20 is in turn reciprocably mounted upon the platform 30. The carriage 20 is thus mounted upon, slidable, and reciprocably movable upon a pair of parallelly disposed rods or shafts $31_1$, $31_2$ which extend across an open rectangular shaped slot 32 within the horizontally disposed platform 30. The platform 30, as will be noted, is mounted via the vertical support structure 33 above the base 92 upon which the carrousel feed tray 90 is rotatably mounted via a vertical spindle or shaft 93 located at the geometric center of the base 92. The shafts $31_1$, $31_2$ form rails upon which the carriage 20 carrying the syringe, or syringe assembly 10 is reciprocably movable via action of the cylinder-piston unit 14 mounted on the upper surface of the platform 30, located as a superstructure above the base 92.

The syringe, or syringe sub-assembly 10 includes a carriage 20, inclusive of a horizontal oriented floorplate 21, and vertically oriented end members $22_1$, $22_2$ mounted perpendicularly one at each end of the floorplate 21. The outer longer edges on each side of the floorplate 21 is provided with parallelly aligned openings which mate with and slide upon the shafts $31_1$, $31_2$ which run the length of the slot 32. The upper portion of the forward vertical end member $22_2$ is provided with a lock assembly $22_{24}$ within which the needle 12 can be, and is rigidly secured. A second, protective needle guide mount 23 is located at a spaced distance in front of the forward vertical end member $22_2$, the base of this member being provided with side openings which mate with and slide upon the shafts $31_1$, $31_2$. The guide mount 23 also includes a central shaft (not shown) which extends rearwardly and fits slidably within an elongate central opening on the floorplate 21 of the carriage 20. The protective needle guide mount 23, and an additional fixed needle guide 24 prevents damage to the needle 12 when the carriage 20 is moved forwardly upon the platform 30 over a major portion of the carriage's movement, and then yields to and permits additional continued movement of the carriage 20, the said central shaft being projected inwardly into the central opening within the floor plate 21, as the dispensing end $12_2$ of the needle 12 is inserted within the septum inlet 120.

The carriage 20 is thus reciprocably mounted via rails located atop the platform 30 and can, via action of the cylinder piston unit 14 be oscillated over the length of the rails 31 to project the dispensing end $12_2$ of the needle 12 into the septum inlet 120, and withdraw same. The valve 13-barrel 11 subassembly, on the other hand, is also reciprocably movable relative to the needle 12 which, relative to carriage 20 is maintained in a fixed position. The valve 13-barrel 11 sub-assembly is movable within carriage 20 to load the barrel 11 of the syringe with a fluid specimen obtained by the probe assembly 60 from a vial, and then to eject same via the dispensing end $12_2$ of the needle 12 as when the dispensing end $12_2$ of the needle 12 has been inserted into the septum inlet 120. The structure of carriage 20 is essentially as follows: the outer edges of the elongated sides of the vertical end walls $22_1$, $22_2$, mounted on floorplate 21 of the carriage 20 are also provided with parallelly mounted guide shafts $25_1$, $25_2$. The outer lower side edges of the valve 13 are thus provided with openings through which are fitted the guide shafts $25_1$, $25_2$, and tubular stop collars $26_1$, $26_2$ of equal preselected length are fitted on the forward sides of each of the guide shafts $25_1$, $25_2$ such that the valve 13, within the forward base of which the barrel 11 of the syringe 10 is fitted, and extended, is slidably or reciprocably movable over a limited distance thereon. The distance of movement of the valve 13-syringe barrel 11 sub-assembly is defined by the point of impingement of the lower rearward face of valve 13 with the forward face of vertical end member $22_1$, and the point of impingement of the lower forward face of valve 13 with the rearwardly projecting terminal ends of tubular stop collars $26_1$, $26_2$. This distance is set to correspond with the distance between the maximum fill position of the bore of the barrel 11 when the valve 13 is in its extreme rearward position upon the carriage 20, and zero fill position when the valve 13 is in its extreme forward position upon the carriage 20. An adjustable stop 27, or stop member of adjustable length, is located on the forward face of the valve 13 to provide fill settings which are of lesser volume than the maximum. The adjustable stop 27 includes a rearward shaft portion threadably mounted on the forward face of the valve 13. Its forward end includes a knurled, knobbed shaft portion threadably engaged within the forward end of the former such that the effective length of the stop 27 can be shortened, or extended, by rotation of the forward knurled, knobbed shaft portion thereof in one direction or the other to move it outwardly from the fixed shaft portion or inwardly toward the fixed shaft portion of the adjustable stop 27. In normal operation, the bore of barrel 11 is always loaded with a maximum charge of a fluid specimen, and the adjustable stop 27 set to deliver less than the maximum charge of the fluid specimen, if desired; as will be subsequently discussed. A maximum charge of a fluid specimen is loaded into the barrel of the syringe by opening the bore of the barrel 11 to its maximum fill position; and this is accomplished by moving the valve 13, from which the barrel 11 of the syringe 10 is extended, to its maximum rearward position upon the carriage 20. The amount of the fluid specimen to be ejected from the bore of the barrel 11, if less than the maximum charge, can then be preselected by setting the adjustable stop 27 so that the valve 13 will move upon the carriage 20 for injection of a specimen a distance less than that required to reach zero fill position. The valve 13-barrel 11 sub-assembly is moved to its maximum rearward position within the carriage 20 for filling via action of low pressure air injector via line A-3 into a cylinder-piston unit 5 located within the rearward face of valve 13 (FIG. 6). This action moves the valve 13-barrel 11 sub-assembly slowly rearwardly while a fluid specimen is loaded into the barrel 11 of the syringe via line 9 (FIGS. 3 and 4) without the formation of bubbles or foam therein.

After filling the barrel 11 of the syringe with a fluid specimen, the next step in the operation of the syringe assembly 10 per se is to transport the syringe assembly across the platform 30 to thrust the dispensing end $12_2$ of the syringe needle 12 into the septum inlet 120 in preparation for the injection of a fluid specimen therein (FIG. 4). This requires movement of the carriage 20 upon which the syringe 10 is transported across the platform 30. The movement of carriage 20 upon the horizonally disposed platform 30 is controlled via the double acting, pneumatic cylinder piston unit 14 mounted upon said platform 30. The forward end of the piston $14_1$ of said cylinder piston unit 14 is thus affixed to an extending side edge of the forward vertical end member $22_2$ of the carriage 22. The carriage 20 is thus moved forwardly by injection of air via line R-2 into the rearward side of the cylinder piston unit 14 which causes extension of the piston $14_1$ from within the housing portion of the cylinder-piston unit 14. Initially, the protective forward needle guide mount 23 is carried forwardly, its forward movement ending on contact thereof with the forwardmost needle guide mount 24 whereupon, as the forward movement of the carriage 20 is continued, the shaft $24_1$ thereof is telescoped within the central opening of the floorplate 21 of the carriage. At this point in time the dispensing end $12_2$ of the needle 12 is thrust into the septum inlet 120, and fluid specimen can be injected from barrel 11 by the forward movement of the valve 13-barrel 11 sub-assembly within the carriage 20. The carriage 20 is moved in the opposite direction upon the platform 30 by injection of air via line R-3 into the forward end of the cylinder piston unit 14, the piston $14_1$ being withdrawn into the housing of the cylinder-piston unit 14.

Figure 5:
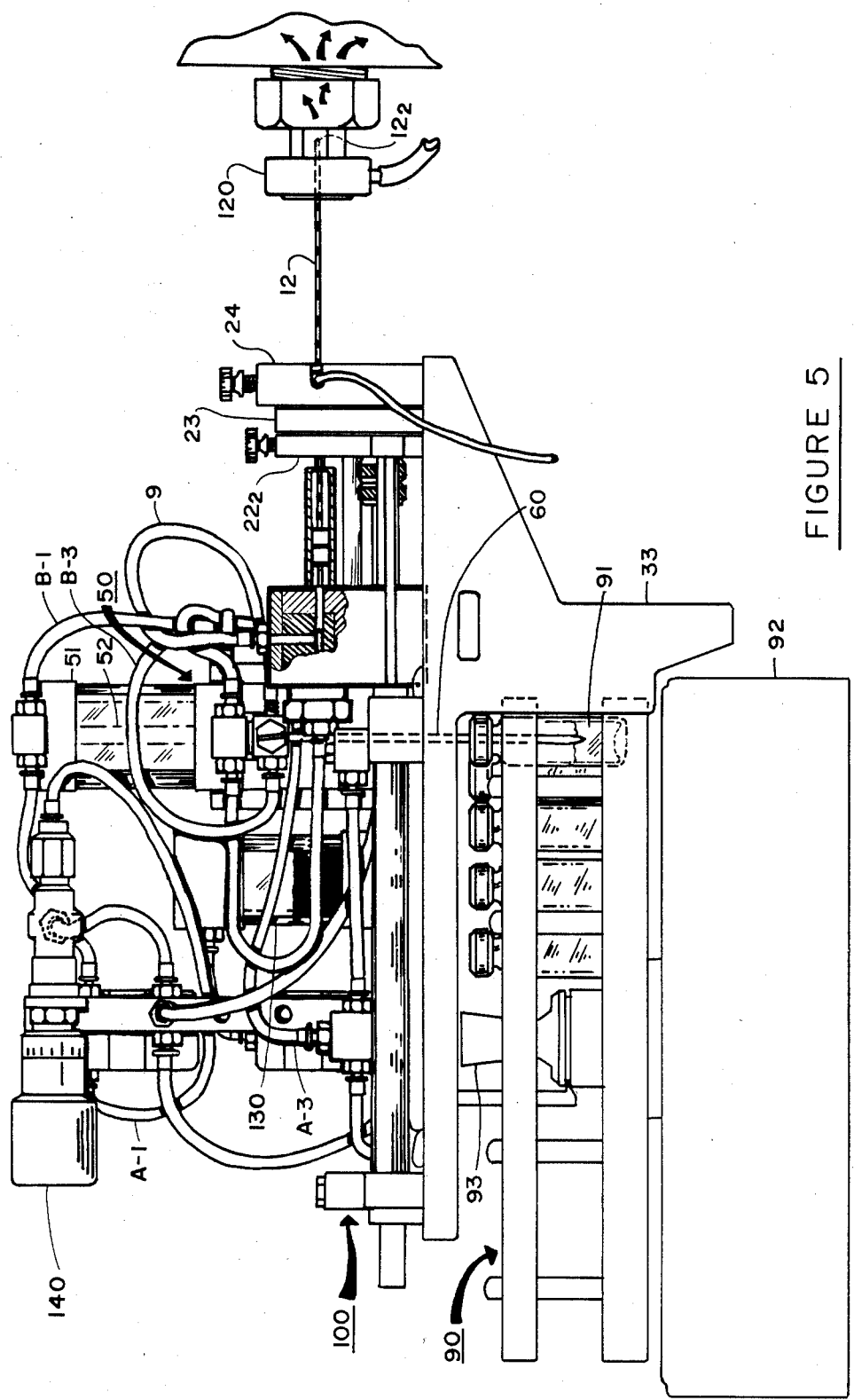
FIG. 5 depicts, via a side elevation view of the automatic fluid injector, initiation of the injection of a fluid specimen from the barrel of the syringe by a continued forward movement of the valve body and barrel portions of the syringe relative to the carriage upon which these elements are transported.

The volume of fluid specimen delivered from the bore of barrel 11 into the septum inlet 120 is determined by the preselected setting of the forward knurled member constituting a portion of the adjustable stop 27. The forward knurled end of the adjustable stop 27 is readily projectable through a central opening within the forward vertical member $22_2$ which presents no limitation to its forward movement. The extent of the forward movement of adjustable stop 27 however can be limited, during the injection portion of the operating cycle, by the guide mount 23 against which the forward knurled end of the adjustable stop 27 can impinge, if sufficiently forwardly extended (FIG. 5). Thus, on the one hand, if the forward knurled member constituting a portion of the adjustable stop 27 is rotated in one direction to limit its extension from the face of the valve 13 and thereby prevent contact thereof with the guide mount 23 in inject position, the entire fluid specimen contents of the barrel 11 can be discharged. On the other hand, an accurately measured fluid specimen in lesser amount can be discharged from the bore of the barrel 11 by adjustment, via rotation of the forward knobbed portion of the adjustable stop 27 in an opposite direction, so that the front end thereof on forward movement of the valve 13-barrel 11 subassembly contacts the guide mount 23; this occurring when the forward movement of guide mount 23 is interrupted by contact with the fixed needle guide 24.

Further, specific reference is made to FIG. 6. It will be observed that the adjustable stop 27, the rearward terminal end of which is threadably engaged with a large antechamber $28_2$ forward of chamber $28_1$ can also be moved inwardly or outwardly, respectfully, to limit or extent, as desired, the distance of movement of the valve 13-barrel 11 sub-assembly within the carriage 20.

The primary function of the valve 13 is to open and close the barrel 11 to the flow of a fluid specimen delivered thereto from a vial via action of the probe assembly 60. When the valve 13 is open, a fluid specimen can be introduced into and passed therethrough to the bore of the barrel 11. When closed, the flow of fluid specimen is interrupted, and on closure to interrupt a previously flowing stream of a fluid specimen a sample of the fluid specimen can be trapped within the bore of the barrel for subsequent injection through the dispensing end $12_2$ of the needle 12. The operation and function of a valved syringe per se as herein employed is described in U.S. Pat. No. 4,044,616 to myself and others, particular reference being made to FIGS. 8 and 9 and to the description thereof at Column 5, lines 32–68 and Column 6, lines 1–17, herewith incorporated and made part of the present disclosure by reference. Referring e.g., to FIG. 6, it will be observed generally that the rearward end of the barrel 11 is snugly fitted, sealed, and contained 25 within the forward face of the valve 13 and movable therewith. The valve 13 is one provided with an on-off position, or one which can be controlled, i.e., opened and closed, in response to a signal, especially an electric signal. The valve 13, as best illustrated by reference to FIG. 6, is consitituted of an outer body or block within which is provided a chamber $13_1$ containing a packing provided with a pair of intersecting openings, a horizontal opening $13_{1A}$ and a vertically oriented opening $13_{1B}$ communicated therewith, the latter providing a connecting conduit through which a fluid specimen can be conveyed via line 9 from the probe assembly 60 of the injector-feed assembly 50 into the barrel 11 of the syringe. The forward portion of the horizontal opening $13_{1A}$ is provided with a nozzle outlet $13_2$ providing a connecting channel through which a fluid specimen can be conveyed via lateral opening $13_{1B}$ into the syringe barrel 11, and the opening $13_{1A}$ as a whole further provides a means, with piston 15, for opening and closing the lateral opening $13_{1B}$ to the flow of a fluid specimen therethrough; or, in other words, a mechanism for opening and closing the valve 13.

The chamber $13_1$ at its opposite end thus further contains a pneumatically actuatable piston 15, the function of which is to open and close the valve 13 in response to an actuating signal, pressurized air entering the chamber via gas entry port $15_1$ to close the valve. The piston 15 thus includes a piston head and stem $15_3$, the latter of which provides the closure element per se of the valve. The piston head, with its circumferential o-ring seals $15_2$, is snugly fitted within the tubular opening within the chamber of the valve 13, and the stem $15_3$ extends into the opening $13_{1A}$ of the tubular packing. The piston 15 can, e.g., be biased in open position by a helical coil spring $15_4$ seated between an outer face of the valve body and inner face of the piston head such that entry of a pressurized gas, e.g., air or nitrogen, via said gas entry port $15_1$ into the valve body will close the valve 13. Thus, the pressure exerted by the helical spring will be overcome and the valve closed by advancing stem $15_3$ into the opening $13_{1A}$ to cut off the flow of a fluid specimen introduced via line 9 to fill the bore of the barrel 11. Conversely, when no pressurized gas is admitted, or is cut-off to the gas entry port $15_1$ the helical spring $15_4$ will be reextended and will cause retraction of the stem $15_3$ from the opening $13_{1A}$ to unblock the lateral side opening $13_{1B}$ to permit the flow of a fluid specimen via line 9 into the bore of the barrel 11.

(B) The purpose of the injector feed assembly 50, with its probe sub-assembly 60, is to pick up a fluid specimen from septum covered vials 91 carried and serially positioned beneath the probe assembly 60 by the carrousel feed tray 90, to withdraw and convey fluid specimen from a vial so positioned to the barrel 11 of the syringe 10. The injector feed assembly 50 includes means, suitably a double acting cylinder piston unit 51, for vertical reciprocation of the probe assembly 60 with which it is an integral part. The lower terminal end of the piston 52 of the cylinder piston unit 51 thus carries a reciprocable hollow probe, or probe assembly 60 which can be projected through the septum of a septum covered vial 91 to withdraw or pick up a fluid specimen therefrom for transfer to the barrel 11 of the syringe 10.

The details of the injector feed assembly 50 is first discussed with reference to FIGS. 1 and 3, and details of the probe assembly 60 are given by reference to FIG. 3A. In FIG. 1 the probe assembly 60 is held in raised position, the piston 52 being withdrawn within the housing or barrel of the cylinder piston unit 51. In FIG. 3 the probe assembly 60 is shown after having been lowered to pierce the septum of a vial 91 for withdrawal of a fluid specimen therefrom for conveyance to the barrel of the syringe 10. The cylinder piston unit 51 per se is conventional. The principle components of the injector feed assembly 50 includes the piston 52 of the cylinder piston unit 51, which carries a probe assembly 60 which can be vertically reciprocated by alternate injection of air, or other pressurized fluid, against the head of the piston contained within the housing or barrel portion of the cylinder piston unit 51. The piston 52, and consequently the probe assembly 60, is reciprocated, first by injection of air via line B-1 into the top end of the housing of the cylinder piston unit 51 to move the piston 52 downwardly, and alternatively into the lower end of the housing via line B-2 to move the piston 52 upwardly. Thus, the septum of a vial 91 transported into position, or on station, beneath the probe assembly 60 is penetrated by downward projection of the probe assembly 60 carried by piston 52 when air is injected via line B-1 into the upper end of the housing of the cylinder piston unit 51. It is withdrawn from a vial 91 via injection of air via line B-2 into the lower end of the housing of the cyclinder piston unit 51.

The structural details of the probe assembly 60, and its function, are best described and illustrated by reference to U.S. Pat. No. 4,044,616, supra, specific reference being made to FIG. 7 and the desscription thereof at Column 8, lines 53–68 and Column 9, lines 1–3 herewith incorporated by reference. The operation of the probe assembly 60, and its function, will be understood by continued reference to FIG. 3, and FIG. 3A. The lower end of probe assembly 60, as shown in FIG. 3, and 3A is projected into a vial 91 which contains a fluid specimen which is to be delivered to the barrel 11 of syringe 10. The probe assembly 60 per se, as shown best by reference to FIG. 3A, is constituted of a pair of concentrically mounted hollow needles; an inner needle $61_1$ contained within a larger needle $61_2$. An annulus between the inner needle $61_1$ and outer needle $61_2$ provides an internal conduit within which a gas, suitably air, under low pressure can be transmitted through an inlet as via line B-3 through a connecting port 62, the gas entering vial 91 via the exit port $61_3$. Since the gas cannot escape from the vial due to the presence of the septum $91_1$, which is held tightly atop the vial by a screw cover $91_2$, the fluid contents of the vial are pressurized by the entering gas, and fluid specimen is forced into the entry port $61_4$, the fluid specimen ascending through the bore of needle $61_1$ and exiting the connecting tubing 9 whereupon it flows through the valve 13 on opening into the barrel 11 of syringe 10.

(C) The function of the carrousel feed tray 90 is to transport fluid specimen filled vials in seriatim one behind the other to a location for pick up and transport of the fluid contents thereof to the syringe barrel 11 by the hy-injector feed assembly 50. The injector feed assembly per se can be of virtually any type, or design as described e.g., in U.S. Pat. Nos. 3,754,443, 3,824,859, 3,885,438, 3,940,995. In a preferred embodiment, as described herein, a carrousel feed tray 90 is provided for conveying a plurality of fluid specimen-containing vials 91. It is constituted of a rotary table containing, or which can contain, a plurality of fluid specimen containing vials 91; the table being rotated about a spindle or shaft 93 located at the geometric center of the base 92. As the vials 91 are serially moved into position beneath the probe assembly 60 of the injector feed assembly 50, the probe 60 is thrust downwardly so that the pointed or tapered end of the outer needle $61_2$ penetrates the septum $91_1$ of a vial in an initial step in preparation for pick up and transport of a fluid specimen to the barrel 11 of the syringe 10.

A feature of this invention relates to the combination which includes means, perferably both pneumatic and hydraulic means, for powering the operations of the (A) syringe, or syringe assembly 10, and (B) the injector feed assembly 50 to assure optimum time periods, and optimum performance for each portion of the total cycle of operation. Preferably the carriage 20 is oscillated across the platform 30 via pneumatic means, suitably via use of the double-acting pneumatically activated cylinder piston unit 14. High pressure air can thus be used to rapidly move the piston $14_1$ in one direction to drive the carriage 20 in its forward direction to insert the dispensing end $12_2$ of the needle 12 into the septum inlet 120, and in an opposite direction to retract the needle 12 by withdrawal of the piston $14_1$ to reverse the direction of movement of the carriage 20. High pressure air is also employed to lower and raise the probe assembly 50 via injection of air into the top end via line B-1 and lower end via line B-2, respectively, of the cylinder piston unit 51 of the injector feed assembly 50. Air, at relatively high pressure is also injected via line A-1 into the top of a hydraulic reservoir 130 to provide the desired pressure upon the oil, and air can be used to open and close the valve 13, viz., via air fed through line A-4 to the piston unit 15 to close the valve 13, and the cutting off of air thereto to open the valve 13. Low pressure air can be passed via line B-3 into the probe assembly 60 to pressurize a vial 91 for conveying a fluid specimen to the barrel of the syringe. Low pressure air is also preferably employed via injection thereof through line A-3 into the piston unit 5 to retract the valve 13-barrel 11 sub-assembly to slowly fill, while avoiding bubble formation, the barrel of the syringe with a fluid specimen supplied via the injector feed assembly 50.

A hydraulic reservoir 130, precision flow needle control valve 140, hydraulic piston units and leads thereto as hereinafter defined constitute the heart of the hydraulic system. Reference is best made to FIG. 6. The precision flow needle control valve 140 is constituted generally of a knurled knob portion 141 rigidly affixed to a shaft 142 which is threadably engaged with, and extended through an axial opening within a tubular body 143. The tubular body 143 of the needle control valve 140 contains a chamber $143_1$, a forward circular opening and rearwardly placed packing $143_2$ through which the tapered or pointed end $142_1$ of the shaft 142 is extended. The tapered end $142_1$ of the shaft 142, when located in a position sufficiently rearwardly of the circular shaped inlet to chamber 143 provides a relatively large opening for the input of hydraulic fluid via hydraulic inlet line H-4, and conversely when the tapered end $142_1$ of the shaft 142 is closely located to the circular shaped inlet to chamber 143 a relatively small opening restricts the flow for the input of hydraulic fluid via hydraulic inlet line $H_4$. Hydraulic fluid from reservoir 130 is thus metered by rotation of the scaled knob 141 in one direction to project the tapered needle end $142_1$ of shaft 142 into the restricted passageway of circular cross-section to restrict oil flow from the input side to the output side of the needle valve 140, and in the opposite direction to withdraw the needle end $142_1$ of the shaft 142 from the circular passageway to permit greater flow from the input side to the output side of the needle valve 140. A metered flow of hydraulic fluid is used in the combination herein described to rapidly close the valve 13 of the valve 13-barrel 11 sub-assembly after the barrel has been filled, and to close the valve 13-barrel 11 sub-assembly upon the needle 12 to inject a fluid specimen from the barrel 11.

An operating cycle is conveniently desscribed again by direct reference to FIGS. 1 through 6, these figures taken in sequence depicting the pick up of a fluid specimen from a septum covered vial and delivery thereof to the barrel of the syringe, or syringe assembly 10, and injection of a preselected quantity of the fluid specimen into the inlet of an analytical instrument, as follows:

(a) Referring first to FIG. 1, the probe assembly 60 of the injector feed assembly 50 is shown in elevated, or raised position, the piston 52 being withdrawn into the housing or barrel of the cylinder piston unit 51. A vial 91 has been delivered to a location beneath the probe assembly 60 via rotation of the carrousel feed tray 90 (via means not shown), on which is carried a plurality of vials 91. The carrousel feed tray 90, at this point in time is now motionless.

The carriage 20, as shown by reference to FIGS. 1 or 2, is in its extreme rearward position upon the horizontal platform 30, the piston 52 of the cylinder piston unit 51 being withdrawn upwardly with its housing. The valve 13 is in its extreme forward position on the carriage 20. In this position, it will be observed that the forward face of the block which forms the valve 13 rests against the tubular collar stops $26_1$, $26_2$ and the forward face of the tubular seal $13_{2A}$ of the projecting nozzle stem $13_2$ abuts the rearward face of the tubular seal $12_1$ on the rearward end of needle 12. The interface of the two tubular seals $13_{2A}$, $12_1$ is at the point indicative of the maximum fill position, though at this point in time there is no space for a fluid specimen within the bore of the barrel 11. The valve 13 at this point in time is closed. The needle 12 is in a fully retracted position.

In this position, hydraulic fluid has thus just closed the syringe via forward movement of the valve 13-barrel 11 sub-assembly within the carriag 20. Hydraulic fluid from the body of fluid in reservoir 130, pressurized by air introduced into the vessel above the fluid body via line A-1, was thus transferred via lines H-1, past solenoid 8 to H-2, and through the T-frame 7 via line H-5 into the nozzle inlet 28 at the lower side of the valve 13. Pressurized hydraulic fluid entering nozzle inlet 28, rigidly affixed to the vertical end wall $22_1$, thus fills the chamber $28_1$ and pushes the valve 13-barrel 11 sub-assembly to its extreme forward position within the carriage 20.

(b) The probe assembly 60 of the injector feed assembly 50, with its concentric needle assembly 61, is projected downwardly, pressurized fluid being injected via line B-1 into the upper end of the cylinder piston unit 51 to move piston 52 downwardly; the piston 52 carrying with it the probe assembly 60.

Air fed into the top of the hydraulic reservoir 130 via line A-1 is now turned off.

Air from a solenoid D (not shown) now causes air to be transmitted via line A-3 into the cylinder piston unit 14, not activating the cylinder piston unit 14 in this instance since the piston $14_1$ of this unit is already retracted. The air transmitted through line A-3 begins to relatively slowly retract the valve 13-barrel 11 sub-assembly within the carriage 20, because the air to cylinder 14 is also directed to piston chamber 5. This movement of the valve 13-barrel 11 sub-assembly ends with the syringe in its standard load position.

Figure 3A:
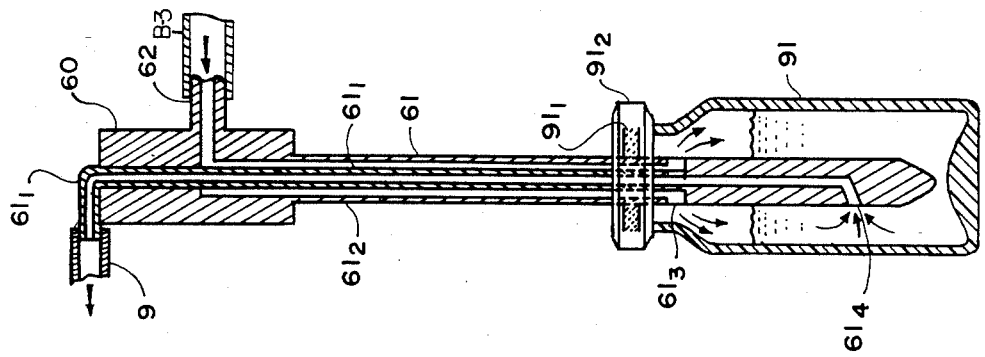
Figure 3:
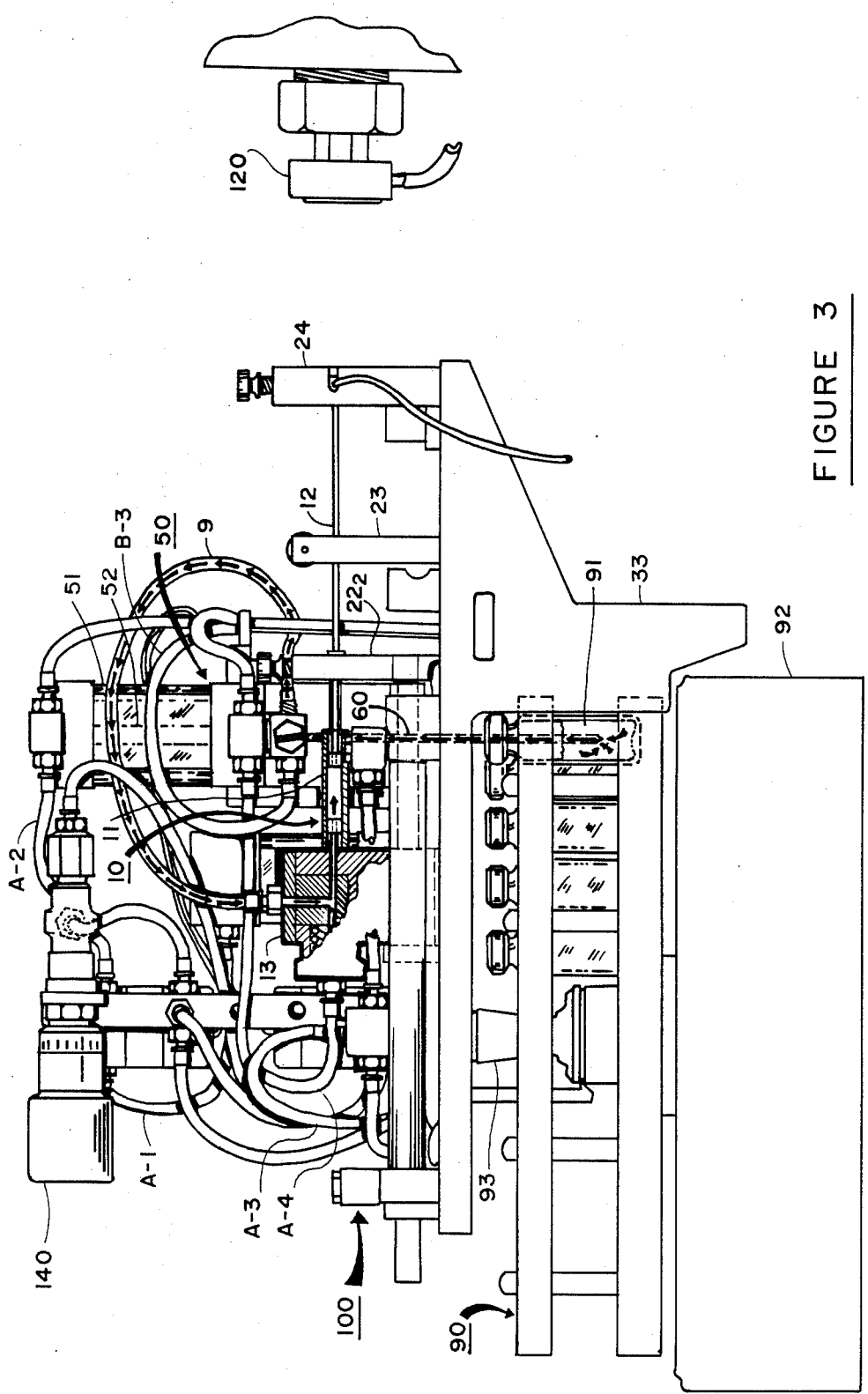
Figure 4:
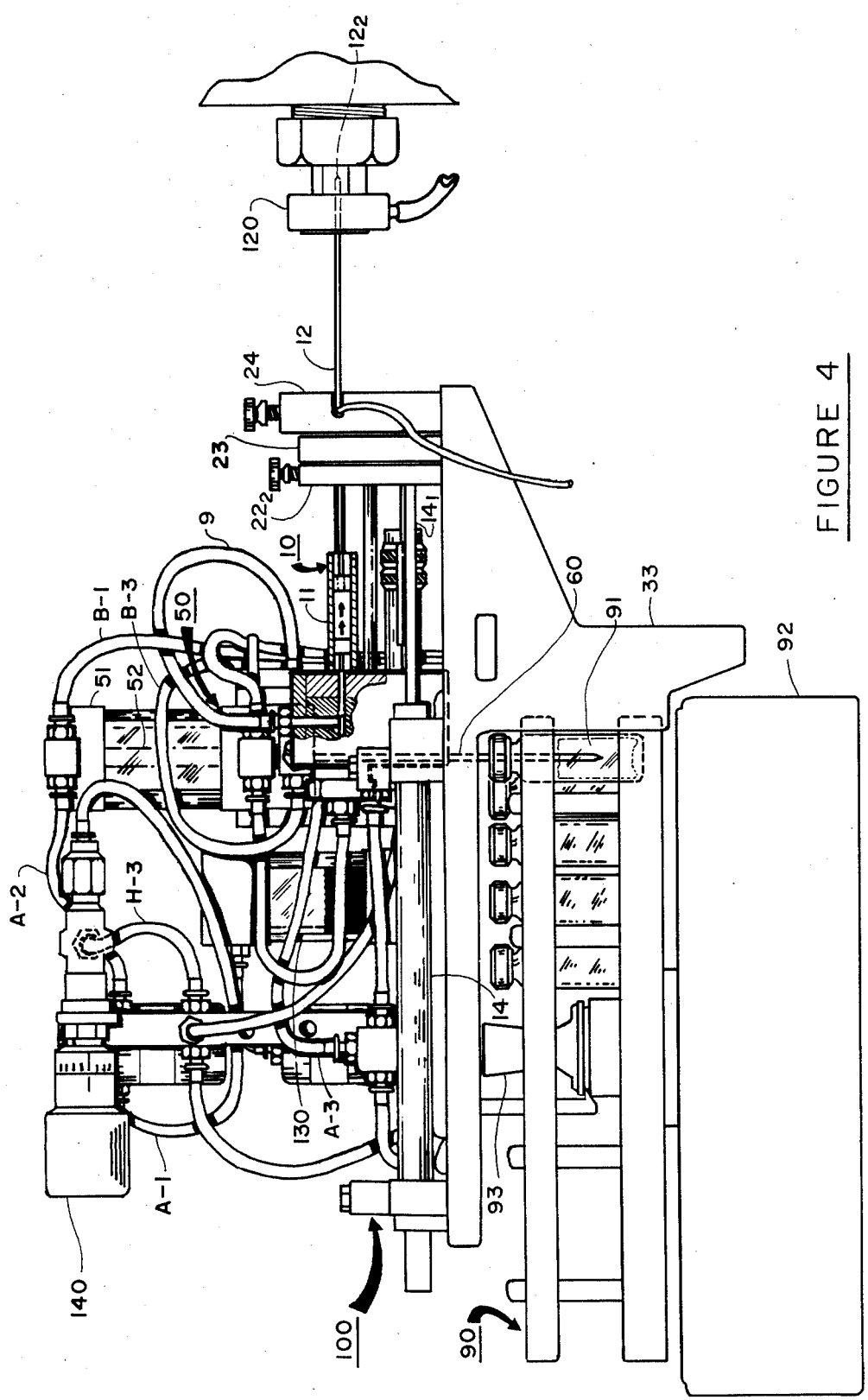
FIG. 4 depicts in partial section, again by means of a side elevation view of the automatic fluid injector, transport of the carriage to its extreme forward position upon the platform, thrust of the dispensing end of the needle of the syringe into a septum inlet, and closure of the valve to cut off the flow of fluid specimen to the syringe from a vial via the probe assembly mechanism.

Reference is made to FIGS. 3 and 3A. The terminal end of the probe assembly 60 near the bottom of its stroke penetrates the septum of a vial 91, a pressurized gas is injected via line B-3 and inlet 62 into the annulus between the pair of probe needles $61_1$, $61_2$, the gas exiting via the opening $61_3$ to pressurize the inside of a vial 91. The fluid specimen of the vial 91, under pressure, is forced via opening $61_4$ into the inner probe needle $61_1$ whereupon it is conveyed via line 9 to the valve 13, which is now opened via cutting off the flow of pressurized air via line A-4 to cause retraction of the valve stem $15_3$ away from the lateral opening $13_{1B}$.

As the valve 13-barrel 11 sub-assembly moves rearwardly upon the carriage 20 the interface between the two seals $13_{2A}$, $12_1$ gradually widens and forms an opening within the barrel which is filled with fluid specimen injected via line 9 into the open valve 13. Because of the very slow movement of the valve 13-barrel 11 sub-assembly rearwardly the opening bore of the barrel 11 is gradually, completely filled without the formation of any bubbles. The filling continues until, e.g., the lower rearward face of the valve 13 comes into contact with the rearward vertical wall $22_1$ of the carriage 20. At this point in time the rearward interface of the seal $12_1$ of needle 12 is at a zero reading, the distance between the interfaces of the two seals providing maximum fill. During this period of rearward movement of valve 13, it will be noted that the needle 12 is maintained in a fixed position; e.g., the needle 12, with 11 its rearward seal $12_1$ remains stationary. The valve 13-barrel 11 sub-assembly and the end seal $13_{2A}$ of nozzle $13_2$ is thus moved relative thereto. With the barrel 11 fixed, the valve 13 is now closed via the action of a solenoid B (not shown) which comes "on" to inject air via line A-4 to the piston unit 15 to close valve 13, and block any further flow of fluid specimen via line 9 in the syringe.

(c) Reference is made to FIG. 4. The carriage 20 is now driven forwardly relatively rapidly via activation of a solenoid C (not shown) which is turned "on" to cause the injection of air via line R-2 into the rearward end of the cylinder piston unit 14, the piston $14_1$ being projected outwardly from its housing. The needle 12 is guided along its path, and protected from bending by the protective needle guide $22_2$ which moves forward with the carriage 20, upon which it is mounted, until it contacts the forward needle guide 23, and thereafter, as forward movement of the carriage 20 is continued, the shaft portion of the needle guide $22_2$ telescopes within the floorplate 21 of the carriage 20, further continuously protecting and guiding the needle 12 as it does so. The movement of the carriage 20 stops after the vertical front wall $22_2$ of the carriage 20 contacts the forward needle guide 23, and the forward needle guide 23 contacts the forwardmost needle guide 24. At this point in time, the dispensing end $12_2$ of the needle 12 is inserted within the inlet 120.

(d) Reference is made to FIG. 5. The valve 13, yet closed, is next brought slowly forwardly within the carriage 20 the barrel 11 telescoping upon the seal end of needle 12 to displace fluid from the bore of the barrel. Solenoid 6 is switched "on" to supply air to the top of reservoir 130 (but solenoid 8 remains inactivated to divert hydraulic fluid through the needle valve 140 via line H-4).

Metered hydraulic fluid leaving the needle valve 140, passes through lines H-3 and H-5 to enter the bottom of the valve 13 via nozzle inlet 28 to initiate movement of the valve 13-barrel 11 sub-assembly such that an accurately measured quantity of the fluid specimen is, in this manner injected from the barrel 11 and through this dispensing end of the needle 12. If less than a full barrel of the fluid specimen is to be injected, the adjustable stop 27 can be set to control the forward distance of movement of the valve 13-barrel 11 sub-assembly upon the carriage 20. To inject the full contents of the barrel 11, the interface of the nozzle seal $13_{2A}$ is brought all the way forward to the zero fill position, and into contact with the rearward interface of the seal $12_1$ of needle 12. To deliver a lesser accurately measured quantity of the fluid specimen from the barrel 11 the adjustable stop is set such that the forward end thereof will contact the guide mount 23 upon contact of the latter with the fixed needle guide 24 during the injection of the operating cycle. The amount of fluid delivered via the dispensing end $12_2$ of the needle 12 into the inlet 120 is thus directly determined by the amount of fluid displaced by the seal end of the needle 12 as the barrel 11 is moved relative thereto, and this can be adjusted by this, or various other mechanical means known to the art. Injection of an accurately measured quantity of a fluid specimen thus accomplished, if desired the valve 13 can again be opened, and the flow path between the probe assembly 60 and needle 12 readily cleaned as with a solvent, or solvents, and dried.

(e) To ready the instrument for the next cycle of operation, solenoid D (not shown) comes "on" at exactly the same time that solenoid C (not shown) is turned "off," this actuating the cylinder piston unit 14 causing it to retract the carriage 20. On actuation of solenoid D (not shown) air is injected into the forward end of cylinder-piston unit 14 to cause withdrawal of piston $14_1$ into its housing. The carriage 20 is thus repositioned in its most rearward position upon the platform 30, as shown with reference to FIG. 1.

Solenoid A (not shown) now is inactivtied, air being injected via line B-2 into the bottom of the cylinder piston unit 51 to retract the probe assembly 60 of the injector feed assembly 50, and return same to its raised position.

At the same time solenoid D (not shown) is activated, solenoid G (not shown) is activated to allow the valve 13-barrel 11 sub-assembly to be retracted to load position in a rapid unmetered manner, as heretofore described, and the air effecting the retraction of the valve 13-barrel 11 sub-assembly is also directed via line A-3 into the piston unit 5. Solenoids B, D and G are now inactivated, leaving the instrument ready to begin a new cycle with rotation of carrousel tray 90 to place a new vial in sample position.

It is apparent that various modifications and changes can be made without departing the spirit and scope of the present invention. The apparatus is constructed of materials substantially inert or nonreactive to the chemical or corrosive action of the fluid specimens to be measured and dispensed. The barrel of the fluid injector is normally constructed of glass, or a plastic or plastic-like material. The barrel is generally scribed with indicia representative of the volume of the bore. The seals and tubing used in the instrument are normally constructed of rubber or plastic, and the rest of the instrument of various metals.

The seals are preferably formed of a rigid or semi-rigid, resilient form of plastic or plastic-like material. The self-lubricated plastics are especially preferred in this capacity, and can also be applied as a laminate or protective film. The polyfluorinated ethylene polymers, notable among which is polytetrafluoroethylene (Teflon), are particularly outstanding. Conventional resilient or plastic-like materials, such as natural or synthetic rubbers can also be employed.

The fluid injector sub-assembly (except for the barrel), the injector feed assembly, particularly the needle and probes, the piston units, and the like, are preferably constructed of metals, e.g., ferrous metals such as iron, iron alloys, steel, stainless steels, and the like; or such metals as aluminum magnesium, brass, copper, bronze, chrome, alloys of these and other metals, and the like.

It is apparent that various changes, such as in the shape, or the absolute or relative dimensions of the parts, materials used, and the like, as well as the suggested mode or particular sequence of withdrawing or delivering fluid specimens, can be made without departing the spirit and scope of the invention, as will be apparent to those skilled in this art.

Having described the invention, what is claimed is:

1. In a fluid injector useful for the measurement and injection of preselected quantities of a fluid specimen into a medium such as an inlet to an analytical instrument which includes the combination of (A) a syringe assembly inclusive of a barrel into which a fluid specimen can be loaded, a needle mounted on an end of the barrel, and means for the displacement of the fluid specimen from said barrel via the dispensing end of the needle into said inlet, (B) an injector feed assembly comprised of a probe sub-assembly inclusive of a pair of hollow needles which provide conduit means for the pick up of said fluid specimen and transport of said fluid specimen to the barrel of said syringe, and (C) a magazine for transporting one or more fluid specimen-containing septum sealed vials for pick up by said pair of hollow needles of said probe sub-assembly for delivery to the barrel of said syringe via thrust of the probe through the septum of a vial, pressurizing the contents of the vial by delivery of gas from a source through a first of said hollow needles of said probe sub-assembly to produce flow of fluid specimen from the vial into the second of the set of hollow needles for transport through the probe sub-assembly to the barrel of the syringe, a platform located adjacent the magazine (C) atop which the syringe assembly (A) is mounted, the improvement wherein the syringe subassembly of the injector feed assembly (A) comprises the combination of (i) a carriage, reciprocably movable upon said platform, which is integral with and carries said syringe assembly which is further characterized as including a valve within the forward face of which said barrel of relatively large diameter is mounted, and integral therewith, and through which a fluid specimen can flow from a vial via direct communication with the second of the hollow needles of said probe sub-assembly when the valve is opened, the barrel filled with the fluid specimen by rearward movement of the valve-barrel sub-assembly relative to the needle, the flow of fluid specimen cut off when the valve is closed, and fluid specimen displaced from the barrel via the dispensing end of the needle when the valve-barrel sub-assembly is moved relative to the barrel, (ii) means for reciprocating the carriage upon the platform for insertion of the dispensing end of the needle of said syringe into the inlet of the analytical instrument, and for retracting the carriage for withdrawal of same from said inlet, and (iii) means for retraction of the valve-barrel sub-assembly relative to the needle on flow through of a fluid specimen from said open valve through the barrel sufficiently slowly to avoid the formation of bubbles within the barrel on filling same with said fluid specimen.

2. The apparatus of claim 1 wherein the platform upon which the carriage is mounted is provided with tracks upon which the carriage can be reciprocated, and the valve-barrel sub-assembly of the syringe assembly per se is reciprocably movable upon the carriage relative to the needle portion thereof which is mounted upon, and maintained in a fixed position relative to the carriage.

3. The apparatus of claim 2 wherein a pneumatic cylinder-piston unit mounted upon the platform constitutes the means for reciprocation of the carriage upon the tracks.

4. The apparatus of claim 2 wherein the carriage per se is provided with tracks upon which the valve-barrel sub-assembly of the syringe is mounted and reciprocably movable.

5. The apparatus of claim 1 wherein the platform upon which the carriage is mounted is provided with an elongate slot and pair of parallel rods running the length of the slot constituting tracks upon which the carriage is integrally mounted and slidable, the carriage is provided with a floorplate and thereabove a pair of parallel rods extending from a rearward vertically oriented end wall to a forward vertically oriented end wall mounted at opposite ends of the floorplate, the valve-barrel sub-assembly is integrally mounted and slidable upon said parallel end walls of the carriage, the needle portion of the syringe assembly is affixed to the front vertical end wall of the carriage, a needle guide through which the needle is extended is mounted in front of the carriage and reciprocably movable upon the tracks within the elongate slot of the platform, and the carriage is reciprocably movable along the tracks within the elongate slot of the platform via a pneumatically actuated cylinder piston unit mounted upon the platform.

6. The apparatus of claim 5 wherein each of the parallel rods mounted across the vertical end walls of the carriage is provided with a tubular collar to limit the distance of movement of the valve-barrel sub-assembly between a zero fluid specimen fill position and a maximum fill position.

7. The apparatus of claim 6 wherein the forward vertical end wall of the carriage is provided with an opening, the forward face of the valve portion of the valve-barrel sub-assembly is provided with a stop of adjustable length extendable through the opening of said carriage forward vertical end wall, a needle guide mount carried on the forward end of the carriage, and fixed needle guide located in a position forward of said carriage needle guide mount which, on abuttment of the stop against the needle guide mount, the forward movement of which is limited by abuttment with the fixed needle guide, can limit the volume of a fluid specimen delivered from the barrel of the syringe via the dispensing end of the needle.

8. The apparatus of claim 5 wherein the valve, on flow of a fluid specimen through the valve, is opened and closed via a pneumatically actuated means.

9. The apparatus of claim 5 wherein the valve-barrel sub-assembly of the syringe assembly, while a fluid specimen is flowing through the open valve, barrel and needle, can be retracted via pneumatically actuated means.

10. The apparatus of claim 5 wherein the valve-barrel sub-assembly of the syringe assembly, while a fluid specimen is flowing through the open valve, barrel and needle can be retracted via pneumatically actuated means, the flow of fluid specimen through the open valve, barrel and needle closed off by closure of the valve via pneumatic means, and the fluid specimen ejected from the barrel and dispensed through the dispensing end of the needle by closure of the valve-barrel sub-assembly upon the fixed needle via metered hydraulic fluid means.

11. The apparatus of claim 1 wherein the probe sub-assembly of the injector feed assembly (B) is comprised of a pair of concentrically mounted hollow needles, an outer tubular needle of relatively large internal diameter and an inner tubular needle a terminal end and at least an adjacent portion thereof being contained within the opening through said outer tubular needle, the inner needle being of sufficiently small outside diameter to form an annulus between the external surface of said inner tubular needle and the internal surface of said outer rigid tubular needle, said annulus being communicated with air inlet means while the opposite end of said inner tubular needle is communicated with the barrel of said syringe, whereby when the terminal end of said outer hollow needle is thrust through the septum of a specimen sealed fluid specimen-containing needle and extended to the bottom of the vial, the vial pressurized by air injected via the air inlet means to the tubular barrel and passed via the annulus between the external surface of said inner tubular needle and the internal surface of said outer tubular needle to convey the fluid specimen via the inner needle to the barrel of the syringe.

12. In a fluid injector useful for the measurement and injection of preselected quantities of a fluid specimen into a medium such as an inlet to an analytical instrument which includes the combination of (A) a syringe assembly inclusive of a barrel into which a fluid specimen can be loaded, a needle mounted on an end of the barrel, and means for the displacement of the fluid specimen from said barrel via the dispensing end of the needle into said inlet, (B) an injector feed assembly comprised of a probe sub-assembly inclusive of a pair of hollow needles which provide conduit means for the pick up of said fluid specimen and transport of said fluid specimen to the barrel of said syringe, and (C) a magazine for transporting one or more fluid specimen-containing septum sealed vials for pick up by said pair of hollow needles of said probe sub-assembly for delivery to the barrel of said syringe via thrust of the probe through the septum of a vial, pressurizing the contents of the vial by delivery of gas from a source through a first of said hollow needles of said probe sub-assembly to produce flow of fluid specimen from the vial into the second of the set of hollow needles for transport through the probe sub-assembly to the barrel of the syringe, the improvement comprising
a platform provided with a track running the length of the platform,
a carriage mounted on said track and slidable thereon,
a syringe assembly mounted on said carriage, including a valve-barrel sub-assembly constituted of a valve within the forward face of which a barrel of relatively large diameter is mounted, and a needle mounted in fixed position upon said carriage one end of which is extended into and sealed within the barrel of said valve-barrel sub-assembly with the other end constituting the dispensing end of the needle, said valve-barrel sub-assembly being reciprocably movable upon said carriage relative to said needle, a conduit connection between the second of the hollow needles of said probe sub-assembly and the valve of said valve-barrel sub-assembly through which a fluid specimen can flow from a vial when the valve is opened, the barrel filled with the fluid specimen by rearward movement of the valve-barrel sub-assembly relative to the needle, the flow of fluid specimen cut off when the valve is closed, and fluid specimen displaced from the barrel via the dispensing end of the needle when the valve-barrel sub-assembly is moved relative to the barrel, pneumatic means associated with said carriage for the reciprocation thereof upon the track of said platform for insertion of the dispensing end of the needle of the syringe assembly into said inlet of the analytical instrument, and withdrawal of same therefrom, pneumatic means associated with the valve-barrel sub-assembly for slowly withdrawing same relative to the needle mounted within the barrel thereof to fill the barrel without the formation of bubbles and foam, and hydraulic metering means associated with the valve-barrel sub-assembly for controlling the rate of forward movement of the barrel-syringe sub-assembly relative to the needle affixed within the barrel thereof to displace a fluid specimen from the barrel via the dispensing end of the needle for injection into said inlet.

13. The apparatus of claim 12 wherein a pneumatic cylinder-piston unit mounted upon the platform constitutes the pneumatic means employed for reciprocation of the carriage upon the track, and a pneumatic cylinder-piston unit integral with the valve portion of the valve-barrel sub-assembly constitutes the pneumatic means employed for loading the syringe assembly with a fluid specimen within the formation of bubbles and foam within the barrel of the syringe assembly.

14. The apparatus of claim 12 wherein the hydraulic metering means associated with the valve-barrel sub-assembly is constituted of a hydraulically actuated cylinder-piston unit located within the valve portion of the valve-barrel sub-assembly, a pressurized reservoir of hydraulic fluid in communication therewith, and an adjustable precision flow needle control valve through which fluid from the reservoir is passed and the flow thereof regulated to that desired prior to passage to the hydraulically actuated cylinder-piston unit.

* * * * *